(12) United States Patent
Von Malmborg et al.

(10) Patent No.: US 8,403,868 B2
(45) Date of Patent: *Mar. 26, 2013

(54) SENSOR AND GUIDE WIRE ASSEMBLY

(75) Inventors: Pär Von Malmborg, Uppsala (SE); Erik Düring, Uppsala (SE); Staffan Karlsson, Uppsala (SE)

(73) Assignee: Radi Medical Systems AB, Uppsala (SE)

(*) Notice: Subject to any disclaimer, the term of this patent is extended or adjusted under 35 U.S.C. 154(b) by 0 days.

This patent is subject to a terminal disclaimer.

(21) Appl. No.: 13/079,961

(22) Filed: Apr. 5, 2011

(65) Prior Publication Data

US 2011/0184317 A1    Jul. 28, 2011

Related U.S. Application Data

(63) Continuation of application No. 10/580,418, filed as application No. PCT/EP2004/052989 on Nov. 17, 2004, now Pat. No. 7,931,603.

(60) Provisional application No. 60/523,689, filed on Nov. 21, 2003.

(51) Int. Cl.
*A61B 5/00* (2006.01)
*A61M 25/00* (2006.01)

(52) U.S. Cl. ..................................... 600/585

(58) Field of Classification Search .......... 600/462, 600/465–466, 468, 480, 486, 488, 561, 585
See application file for complete search history.

(56) References Cited

U.S. PATENT DOCUMENTS

| RE35,648 E | 11/1997 | Tenerz et al. |
|---|---|---|
| 5,891,114 A | 4/1999 | Chien et al. |
| 5,964,714 A * | 10/1999 | Lafontaine ............... 600/561 |
| 6,112,598 A | 9/2000 | Tenerz et al. |
| 6,336,906 B1 | 1/2002 | Hammarström et al. |
| 6,881,194 B2 | 4/2005 | Miyata et al. |
| 7,117,703 B2 | 10/2006 | Kato et al. |
| 7,153,277 B2 | 12/2006 | Skujins et al. |
| 2003/0088263 A1 | 5/2003 | Bonnette et al. |
| 2003/0125641 A1 | 7/2003 | Jafari et al. |

FOREIGN PATENT DOCUMENTS

| EP | 0 200 919 A1 | 11/1986 |
|---|---|---|
| EP | 0 419 277 A1 | 3/1991 |
| EP | 1 120 127 A1 | 8/2001 |
| EP | 1 243 283 A2 | 9/2002 |
| JP | 2003-265617 A | 9/2003 |

\* cited by examiner

*Primary Examiner* — Jeffrey G Hoekstra
*Assistant Examiner* — H. Q. Nguyen
(74) *Attorney, Agent, or Firm* — Foley & Lardner LLP

(57) ABSTRACT

A guide wire assembly includes a proximal end portion, a distal portion comprising a coil, a hollow stranded wire extending towards the distal portion, and a core wire. The guide wire assembly is characterized in that a proximal tube is provided, which extends from the proximal end portion to a proximal end of the hollow stranded wire such that the hollow stranded wire is directly joined to the proximal tube. The core wire extends into the distal portion and does not extend into the proximal tube. An entire length of the hollow stranded wire is in a range of 7.5 to 22.5% of an entire length of the guide wire assembly.

16 Claims, 2 Drawing Sheets

SENSOR AND GUIDE WIRE ASSEMBLY

CROSS REFERENCE TO RELATED APPLICATIONS

The present application is a continuation application of U.S. application Ser. No. 10/580,418, filed May 22, 2006, which is the National Stage of Application No. PCT/EP2004/052989 filed on Nov. 17, 2004, which is based upon and claims the benefit of priority from U.S. Provisional Application No. 60/523,689, filed Nov. 21, 2003, the entire contents of all of which are incorporated herein by reference.

FIELD OF THE INVENTION

The present invention relates generally to sensor and guide wire assemblies, in which a sensor element is mounted at the distal end of a guide wire for intravascular measurements of physiological variables in a living body, and in particular to the design and construction of the guide wire. The present invention also relates to a hollow stranded wire for a sensor and guide wire assembly as well as a method of modifying the mechanical properties of the hollow stranded wire.

BACKGROUND OF THE INVENTION

Sensor and guide wire assemblies in which a sensor is mounted at the distal end of a guide wire are known. In U.S. Pat. Re. 35,648, which is assigned to the present assignee, an example of such a sensor and guide wire assembly is disclosed, where a sensor guide comprises a sensor element, an electronic unit, a signal transmitting cable connecting the sensor element to the electronic unit, a flexible tube having the cable and the sensor element disposed therein, a solid metal wire, and a coil attached to the distal end of the solid wire. The sensor element comprises a pressure sensitive device, e.g. a membrane, with piezoresistive elements connected in a Wheatstone bridge-type of arrangement mounted thereon.

The above-mentioned solid metal wire, also called the core wire, extends from the distal end of the sensor guide to the proximal portion, where a male connector is arranged, and determines the overall mechanical properties, such as flexibility, torqueability and pushability, of the sensor guide. Sensor and guide wire assemblies for intravascular measurements are generally long, e.g. 100-300 cm, and have a small diameter, e.g. 0.35 mm. Thus, to provide the necessary stiffness and pushability, the solid metal wire must occupy a large portion of the available space inside the flexible tube, thereby leaving a very limited space for the sensitive signal transmitting conductors.

A different solution is suggested in a Japanese patent application, which is published under no. JP 2003-265617 and which discloses a sensor and guide wire assembly that has no core wire. The overall mechanical properties are instead provided by a hollow stranded wire, inside which electrical leads extend. Such a hollow stranded wire is, for example, sold by Asahi Intecc Co., Ltd. under the trademark Actone™. Besides a distal portion of the guide wire, where a pressure sensor is arranged inside a metallic casing, the hollow stranded wire extends along the length of the sensor guide. No flexible tube is therefore present in this sensor and guide wire assembly.

Although the latter way of constructing a sensor and guide wire assembly, with a hollow stranded wire and without a flexible proximal tube, could work in practise, the mechanical properties of the sensor guide can be improved.

SUMMARY OF THE INVENTION

An object of the present invention is to provide a new and improved design for a sensor and guide wire assembly which exhibits better mechanical performance when maneuvered in small and tortuous vessels.

Another object of the present invention is to provide methods for varying the stiffness of a sensor guide manufactured according to the present invention.

These objects are achieved with sensor and guide wire assembly and by a hollow stranded wire according to the independent claims.

Preferred embodiments are set forth by the dependent claims.

According to one embodiment of the invention, a sensor and guide wire assembly comprises a proximal male connector whose distal end is connected to a proximal tube, a hollow stranded wire connected to the distal end of the proximal tube, a jacket which is connected to the distal end of the hollow stranded wire and which accommodates a sensor element, a distal coil connected to the distal end of the jacket and provided with a distal tip, and at least one electrical lead connecting the sensor element to the proximal male connector. The hollow stranded wire extends along a restricted length of the sensor and guide wire assembly, and determines—together with the proximal tube—the overall mechanical properties of the sensor guide.

In another embodiment of a sensor and guide wire assembly, the sensor element is arranged inside a hollow stranded wire, i.e. in this embodiment there is no jacket provided.

The stiffness and other characteristics of a sensor guide according to the invention can be varied by modifying the hollow stranded wire in different ways. To make the hollow stranded wire more flexible, its diameter can be reduced and/or one or several strands can be removed. To make the hollow stranded wire stiffer, neighbouring strands can be joined.

DETAILED DESCRIPTION OF THE INVENTION

As outlined above, sensor and guide wire assemblies are known which comprise a proximal tube. The proximal tube extends from a proximal male connector to a jacket, inside which a sensor element is arranged. As an alternative, a proximal tube can extend from a proximal male connector to a coil, which, in turn, is connected to such a jacket. A sensor and guide wire assembly of this type comprises further a core wire, which extends along essentially the entire length of the sensor and guide wire assembly. The core wire is thereby longer than the proximal tube, and extends from the proximal male connector, through the jacket, and to the distal tip of the sensor guide. A sensor assembly with this design is, for example, disclosed in the U.S. Pat. Re. 35,648.

As also explained before, sensor and guide wire assemblies have been suggested wherein a hollow stranded wire extends from a proximal male connector to a distal portion where a sensor element is arranged inside a jacket. The hollow stranded wire provides the sensor guide with the mechanical properties, such as stiffness, torqueability and flexibility, that are necessary for the practical use in tortuous vessels. This type of sensor assembly is disclosed in the Japanese patent publication JP 2003-265617. According to this publication no core wire is present in the hollow stranded wire; and it should in particular be noted that the application JP 2003-265617 does not suggest the use of a proximal tube in combination with a hollow stranded wire.

For the purpose of the present invention, it should be emphasized that the mechanical properties of a guide wire having a sensor element mounted at a distal portion thereof are crucial in the practical use of the sensor and guide wire assembly in a medical operation. According to the present invention it has been found that the incorporation of a hollow stranded wire in a sensor and guide wire assembly can improve the flexibility that is necessary for maneuvering in small and tortuous vessels. In contrast to the teaching of the above-mentioned JP 2003-265617, this hollow stranded wire should, however, not extend along a major portion of the length of the sensor guide, but should instead only constitute a minor longitudinal portion of the sensor guide. With this design, the performance of the sensor guide regarding, for example, its pushability and torqueability is improved in comparison with a sensor guide comprising a hollow twisted wire that extends from the proximal male connector to the distal portion where the sensor element is arranged. In short, the inventors of the present invention have realized that it is not necessary to have a hollow stranded wire that extends along essentially the whole sensor assembly, and that the mechanical properties instead are improved if a proximal tube is provided such that a hollow stranded wire only constitutes a minor portion of the sensor guide.

Figure 1:
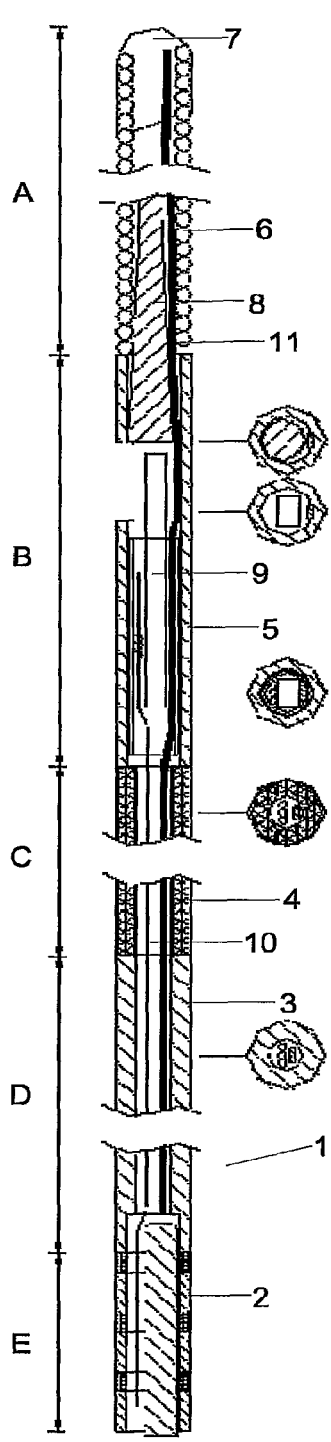
FIG. 1 illustrates schematically a first embodiment of a sensor and guide wire assembly according to the present invention.

FIG. 1 illustrates schematically a first embodiment of a sensor and guide wire assembly 1 according to the present invention. The sensor assembly 1 comprises a proximal portion 2 comprising a male connector, a flexible proximal tube 3, a hollow stranded wire 4, a jacket or sleeve 5, a coil 6 having a tip 7, a distal core wire 8, and a sensor element 9, which is connected to the male connector by at least one electrical lead 10. In use, the male connector in the proximal portion 2 is inserted into a corresponding female connector (not shown in the figure), such that measurement signals from the sensor element 9 can be displayed as curves or numbers on a suitable display unit (not shown in the figure). The sensor assembly 1 comprises further a so-called safety wire 11, which is attached in the tip 7 and extends preferably to the proximal connector 2. In case of an accidental break of the sensor assembly 1 when, for example, a doctor tries to push the sensor assembly 1 through a sharp bend in an artery of a patient, the safety wire 11 will make it possible to retrieve all parts of the sensor assembly 1 from the patient's artery. The safety wire 11 is also helpful during manufacturing of the sensor assembly 1 in that the safety wire 11 can act as a guide when the different parts are assembled and threaded over each other. The safety wire 11 may alternatively have a shorter extension along the sensor assembly, typically from the tip 7 to the jacket 5.

In FIG. 1, the capital letters A to E represent the length of the different sections of the sensor guide, and the following intervals should represent exemplifying but realistic length of the respective sections:

A=length of tip section=2-3 cm
B=length of sensor section=1-3 mm
C=length of flexible section=25-40 cm
D=length of tube section=135-300 cm
E=length of connector section=10-40 mm It should in particular be noted that the length of the flexible section C is rather small in comparison with the total length of the sensor guide. This section C is made up of a hollow stranded wire, for example the hollow stranded wire sold by Asahi Intecc Co., Ltd. under the trademark Actone™. Such a hollow stranded wire has high torque transmission and high kink resistance.

It can further be seen that the flexible tube constitutes the major portion of the length of the sensor guide. Such a flexible tube can be made from stainless steel and is, for example, described in the above-mentioned U.S. Pat. Re. 35,648. It should, however, be noted that—in contrast to the disclosure of Re 35,648—there is no core wire present in the proximal portion of a sensor and guide wire assembly according to the present invention. This means that the walls of the flexible tube can be made thicker without adversely limit the space available for the sensitive electrical lead(s) extending from the sensor element to the proximal connector.

The other parts of the sensor assembly 1, e.g. the male connector, the jacket 5, the coil 6 with the tip 7, the sensor element 9 and the least one lead 10, are all of constructions that are well-known to a person skilled in the art, and are therefore not described further herein. It could, however, be noted that the core wire 8 only extends in the very distal portion of the sensor guide 1, which is in contrast the previously known designs.

Figure 2:
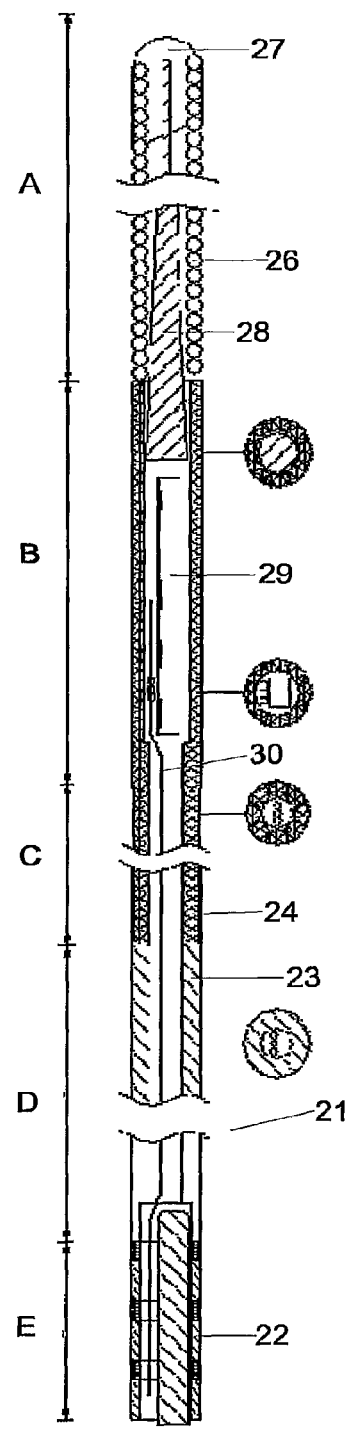
FIG. 2 illustrates schematically a second embodiment of a sensor and guide wire assembly according to the present invention.

A second embodiment of a sensor and guide wire assembly 21 is illustrated in FIG. 2. The sensor assembly 21 comprises a proximal portion 22 comprising a male connector, a flexible proximal tube 23, a hollow stranded wire 24, a coil 26 having a tip 27, a distal core wire 28, and a sensor element 29, which is connected to the male connector in the proximal portion 22 by least one electrical lead 30. The sensor assembly 21 of FIG. 2 differs from the sensor assembly 1 of FIG. 1 in that there is no jacket or sleeve provided. The sensor element 29 is instead arranged within the hollow stranded wire 24. To improve the communication between the sensor element 29 and the ambient medium, e.g. blood, one or several strands could be removed from a portion of the hollow stranded wire 24. In the embodiment shown in FIG. 2, there is no safety wire provided, but it should be understood that such a safety wire could be provided also for this embodiment. It should further be noted that a portion of the hollow stranded wire 24 (i.e. the portion marked with C) has been made more flexible by reducing the diameter of the hollow stranded wire 24 in this section C in comparison with the section marked with B, in which the sensor element 29 is located.

Figure 3:
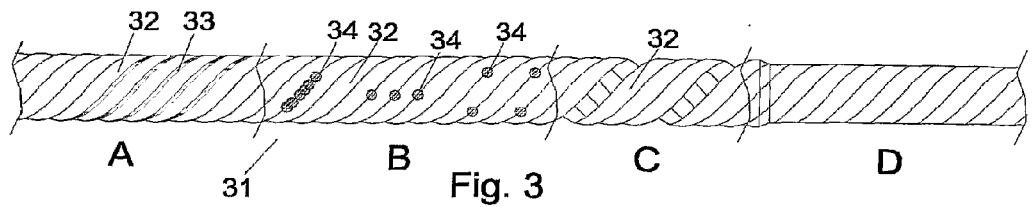
FIG. 3 illustrates different ways of modifying the mechanical characteristics of a hollow stranded wire which is part of a sensor and guide wire assembly according to the present invention.

As suggested above, the properties, e.g. the stiffness, of a hollow stranded wire can be modified in different ways, and in FIG. 3 examples of how this could be accomplished are illustrated. A hollow stranded wire 31 shown in FIG. 3 has been divided into four sections A to D, with each section showing a respective type of modification. In section A, the stiffness of a section of the hollow stranded wire 31 has been increased by gluing together neighbouring strands. The strands are marked with reference number 32, whereas the intermediate glue is marked with 33. As an alternative, the strands could be soldered or welded together along a length thereof.

Another way of increasing the stiffness of the hollow stranded wire 31 is shown in section B, where adjacent strands 32 have been inter-locked with welds 34. The weld spots can provided in different configurations, as shown in the figure.

Section C illustrates how the stiffness the hollow stranded wire 31 can be reduced by removing one or several strands 32. One or several strands 32 can be removed in a restricted portion of the hollow stranded wire 31.

Another way of decreasing the stiffness of the hollow stranded wire 31 is shown in section D, where the outer diameter of the hollow stranded wire 31 has been reduced. This can be accomplished with different methods such as crimping or grinding.

As mentioned several times before, a sensor guide according to the present invention comprises both a hollow stranded wire and a flexible proximal tube—which is in contrast to the sensor guides suggested in the prior art. Apparently, the hollow stranded wire and the proximal tube has to be joined together in order to have sensor guide in which a torque can be transferred from the proximal portion to the most distal portion, something that obviously is necessary in a medical operation. In FIGS. 4a-e several different joint options are depicted.

Figure 4A:
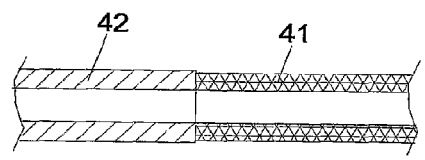
FIGS. 4*a-e* show different type of joints for joining a proximal tube to a hollow stranded wire in a sensor and guide wire assembly according to the invention.

FIG. 4a shows the perhaps simplest way of joining a hollow stranded wire 41 to a proximal tube 42. This is a so-called butt joint, in which the flat end of the hollow stranded wire 41 abuts an opposing flat end of a proximal tube 42. The ends can be welded, soldered or glued together.

Figure 4D:
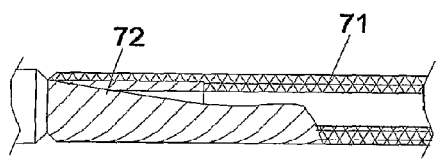
Figure 4B:
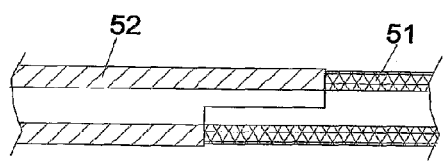

In FIG. 4b a so-called lap joint is illustrated, wherein the end of a hollow stranded wire 51 has been cut such that one end portion protrudes longer than another end portion. The end of a proximal tube 52 has been cut in the corresponding way, with one end portion protruding longer than another end portion. A welded, soldered or glued joint with overlapping end portions can thereby be formed, as seen in FIG. 4b.

Figure 4E:
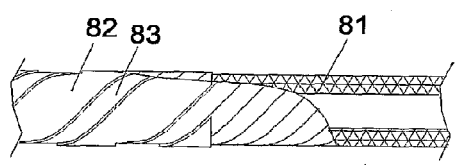
Figure 4C:
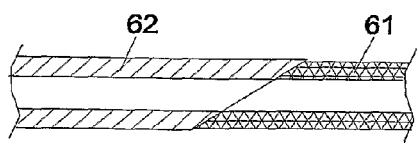

Another type of lap joint is shown in FIG. 4c, where the end of a hollow stranded wire 61 has been chamfered. The opposing end of a proximal tube 62 has been chamfered in the corresponding way, such that the two chamfered ends fit to each other and can be joined by welding, soldering or gluing.

FIG. 4d illustrates a more elaborated type of lap joint, where the end portion of a proximal tube 72 has been given a reduced outer diameter, while an opposing end portion of a hollow stranded wire 71 has been provided with an enlarged inner diameter. It is thereby possible to thread the end portion of the hollow stranded wire 71 over the end portion of the proximal tube 72, whereupon the ends can be welded, soldered or glued together. The opposite way of creating a similar lap joint is also possible, i.e. by having a wire portion with reduced outer diameter and a tube portion with enlarged inner diameter.

In FIG. 4e an inter-locking joint is shown. Here, an end portion of a proximal tube 82 has been provided with helical grooves 83, in which strands of a hollow stranded wire 81 fit. The end portion of the hollow stranded wire 81 can thereby be threaded into the end portion of the proximal tube 82. The joint can then be further secured by welding, soldering or gluing.

In accordance with an alternative embodiment of the present invention the proximal tube has been omitted and the hollow stranded wire has an extension from the proximal end portion to the distal portion of the sensor and guide wire assembly. Here the distal portion includes or does not include a jacket or sleeve. The necessary mechanical characteristics obtained by the proximal tube in the above embodiments is obtained by this alternative embodiment by modifying the mechanical properties along the assembly as described above, e.g. by joining sections of neighbouring strands and/or by removing one or several strands and/or by reducing the diameter of the hollow stranded wire.

Furthermore, and in combination with any of the embodiments discussed above, still other alternatives of modifying the mechanical properties along the assembly may be achieved by performing any procedure of the following:

Laser welding strands of the wire at predefined positions.
Filling predefined parts of the hollow stranded wire by a suitable material, e.g. silicone or a suitable glue.
Crimping a crimping tube, of e.g. silicone or polyurethane, over predefined parts of the wire.
Varying the number of strands along the wire.
Vary the thicknesses of the strands of the wire.

Although the present invention has been described with reference to specific embodiments, also shown in the appended drawings, it will be apparent for those skilled in the art that many variations and modifications can be done within the scope of the invention as described in the specification and defined with reference to the claims below.

The invention claimed is:

1. A guide wire assembly, comprising:
   a proximal end portion;
   a distal portion comprising a coil;
   a hollow stranded wire extending towards the distal portion;
   a proximal tube extending from the proximal end portion to a proximal end of the hollow stranded wire such that the hollow stranded wire is directly joined to the proximal tube; and
   a core wire, wherein the core wire extends into the distal portion and does not extend into the proximal tube,
   wherein an entire length of the hollow stranded wire is in a range of 7.5 to 22.5% of an entire length of the guide wire assembly.

2. A guide wire assembly according to claim 1, wherein the core wire does not extend through the entire length of the hollow stranded wire.

3. A guide wire assembly according to claim 1, wherein the core wire does not extend into the hollow stranded wire.

4. A guide wire assembly according to claim 1, further comprising a jacket and a sensor element arranged inside the jacket, wherein the distal portion is joined to the jacket, and the hollow stranded wire is directly joined to the jacket.

5. A guide wire assembly according to claim 4, wherein the core wire does not extend into the hollow stranded wire.

6. A guide wire assembly according to claim 4, wherein the core wire terminates at and extends from the jacket where the sensor element is provided to a distal tip of the guide wire assembly.

7. A guide wire assembly according to claim 1, further comprising a safety wire extending from the proximal end portion to a distal tip of the guide wire assembly.

8. A guide wire assembly according to claim 1, wherein the proximal tube and the hollow stranded wire are joined together by one of a butt joint, a lap joint, and an inter-locking joint.

9. A guide wire assembly according to claim 1, wherein mechanical properties of the hollow stranded wire have been modified by joining sections of neighboring strands.

10. A guide wire assembly according to claim 1, wherein mechanical properties of the hollow stranded wire have been modified by removing one or more strands.

11. A guide wire assembly according to claim 1, wherein mechanical properties of the hollow stranded wire have been modified by reducing a diameter of the hollow stranded wire.

12. A guide wire assembly according to claim 1, wherein mechanical properties of the hollow stranded wire have been modified by filling predefined parts of the hollow stranded wire with a predetermined material.

13. A guide wire assembly according to claim 12, wherein the predetermined material is silicone or a glue.

14. A guide wire assembly according to claim 1, wherein mechanical properties of the hollow stranded wire have been modified by crimping a crimping tube over a predefined part of the hollow stranded wire.

15. A guide wire assembly according to claim 14, wherein the crimping tube is made of silicone or polyurethane.

16. A guide wire assembly according to claim 1, further comprising another core wire, wherein the another core wire extends through a portion of the proximal end portion.

* * * * *